United States Patent [19]

Youssefyeh et al.

[11] Patent Number: 4,686,295
[45] Date of Patent: Aug. 11, 1987

[54] N-CARBOXY ANHYDRIDE INTERMEDIATES

[75] Inventors: Raymond D. Youssefyeh, Tarrytown; Jerry W. Skiles, Tuckahoe, both of N.Y.; John T. Suh, Greenwich, Conn.; Howard Jones, Ossining, N.Y.

[73] Assignee: USV Pharmaceutical Corporation, Fort Washington, Pa.

[21] Appl. No.: 472,551

[22] Filed: Mar. 7, 1983

[30] Foreign Application Priority Data

Mar. 10, 1982 [CA] Canada .................................. 398031
Mar. 15, 1982 [CA] Canada .................................. 398374

[51] Int. Cl.[4] .......................................... C07D 263/44
[52] U.S. Cl. .................................... 548/226; 544/60;
544/137; 546/146; 546/168; 546/209; 546/275;
548/200; 548/227
[58] Field of Search ................... 544/60, 137; 546/168,
546/146, 209, 275; 548/227, 200, 226;
260/998.2

[56] References Cited

U.S. PATENT DOCUMENTS

| | | |
|---|---|---|
| 1,375,949 | 4/1921 | Altwegg et al. ...................... 548/227 |
| 2,327,162 | 9/1943 | Baldwin et al. ...................... 548/227 |
| 2,516,145 | 7/1950 | Prichard ................................ 548/227 |
| 2,644,808 | 7/1953 | Brubaker et al. .................... 548/227 |
| 3,671,239 | 6/1972 | Zweig ................................... 548/227 |
| 4,160,712 | 7/1979 | Saari et al. ........................... 548/227 |
| 4,267,344 | 5/1981 | Halstrom et al. ................... 548/227 |
| 4,496,541 | 1/1985 | Huang et al. ...................... 260/998.2 |
| 4,496,542 | 1/1985 | Skiles et al. ............................. 514/2 |
| 4,558,038 | 12/1985 | Skiles et al. ...................... 260/998.2 |

FOREIGN PATENT DOCUMENTS

| | | | |
|---|---|---|---|
| 61768 | 10/1982 | European Pat. Off. ............ 548/227 |
| 1563487 | 5/1969 | France ................................. 548/227 |
| 2502614 | 10/1982 | France ................................. 548/227 |

*Primary Examiner*—George F. Lesmes
*Assistant Examiner*—S. A. Gibson
*Attorney, Agent, or Firm*—Scully, Scott, Murphy & Presser

[57] ABSTRACT

This invention relates to new compounds of the formula

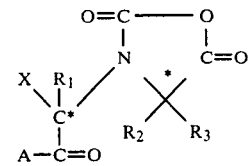

wherein

A is a hydroxy, lower alkoxy, lower alkenoxy, diloweralkylamino lower alkoxy, acylamino lower alkoxy, acyloxy, lower alkoxy, aryloxy, arloweralkyloxy, amino, loweralkylamino, diloweralkylamino, aryloweralkylamino, hydroxyamino, or substituted aryloxy, or substituted arloweralkoxy wherein the substituent is methyl, halo or methoxy;

$R_1$, $R_2$, and $R_3$ are each hydrogen, lower alkyl, lower alkenyl, lower alkynyl, aryl, fused aryl-cycloalkyl, aralkyl, cycloalkyl, heterocyclic, substituted alkyl, alkenyl, or alkynyl groups in which the substituents are hydroxy, alkoxy, halo, amino, aminoalkyl, alkylamino, mercapto, or alkylmercapto, substituted cycloalkyl groups in which the substituents are alkyl, halo, haloalkyl, hydroxy, alkylamino, nitro or trifluoromethyl, and substituted aryl and heterocyclic groups in which the substituents are alkyl, hydroxy, alkoxy, hydroxyalkyl, halo, mercapto, alkylmercapto, mercaptoalkyl, haloalkyl, amino, alkylamino, aminoalkyl, nitro, methylenedioxy, or trifluoromethyl;

X is hydrogen, alkyl, alkenyl or alkynyl of up to about 20 carbon atoms, aryl or aryl lower alkyl containing from about 7 to about 12 carbon atoms, heterocyclic or heterocyclic lower alkyl cycloalkyl or cycloalkylalkyl containing up to about 20 carbon atoms, or of the formula:

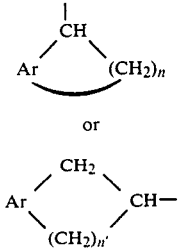

wherein
n=2, 3 or 4;
n'=1, 2 or 3; and
Ar is arylene or mono- or di- substituted arylene in which the substituent is halo, $CF_3$, lower alkyl, OH, lower alkoxy, mercapto, amino or sulfanyl. These compounds are important intermediates in the syntheses of dipeptides which are useful in the treatment of hypertension and are effective as inhibitors of angiotensin converting enzymes.

11 Claims, No Drawings

N-CARBOXY ANHYDRIDE INTERMEDIATES

This invention relates to new intermediate N-carboxy anhydrides useful for the preparation of valuable new therapeutic agents.

The valuable new therapeutic agents are dipeptides which are particularly useful in the treatment of hypertension and are effective as inhibitors of angiotensin converting enzyme. A particularly effective class of such dipeptides are compounds of the formula:

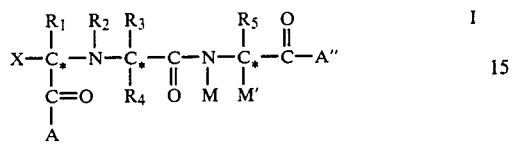   I wherein

A and A″ are independently hydroxy, lower alkoxy, lower alkenoxy, diloweralkylamino lower alkoxy, acylamino lower alkoxy, acyloxy lower alkoxy, aryloxy, arloweralkyloxy, amino, loweralkylamino, diloweralkylamino, aryloweralkylamino, hydroxyamino, or substituted aryloxy, or substituted arloweralkoxy wherein the substituent is methyl, halo or methoxy;

$R_1$, $R_2$, $R_3$, $R_4$ and $R_5$ taken separately are each hydrogen, lower alkyl, lower alkenyl, lower alkynyl, aryl, fused aryl-cycloalkyl, aralkyl, cycloalkyl, heterocyclic, substituted alkyl, alkenyl, or alkynyl groups in which the substituents are hydroxy, alkoxy, halo, amino, aminoalkyl, alkylamino, mercapto, or alkylmercapto, substituted cycloalkyl groups in which the substituents are alkyl, halo, haloalkyl, hydroxy, alkylamino, nitro or trifluoromethyl, and substituted aryl and heterocyclic groups in which the substituents are alkyl, hydroxy, alkoxy, hydroxyalkyl, halo, mercapto, alkylmercapto, mercaptoalkyl, haloalkyl, amino, alkylamino, aminoalkyl, nitro, methylenedioxy, or trifluoromethyl;

$R_1$ and $R_2$ when taken together with the carbon and nitrogen to which they are respectively attached and $R_2$ and $R_3$ when taken together with the nitrogen and carbon to which they are respectively attached form an N-heterocyclic containing from 3 to 5 carbon atoms or 2 to 4 carbon atoms and a sulfur or nitrogen atom;

M is hydrogen, alkyl, alkenyl, alkynyl, cycloalkyl, cycloalkyl-alkyl, polycycloalkyl, polycycloalkyl-alkyl, aryl, aralkyl, heteroaryl, heteroaryl-alkyl, heterocycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylaminoalkyl, dialkylaminoalkyl;

M′ is hydrogen, loweralkyl, cycloalkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl mercapto lower alkyl;

M and M′ when taken together form an alkylene bridge of from 2 to 5 carbon atoms; an alkylene bridge of from 2 to 5 carbon atoms and one sulfur atom; an alkylene bridge of from 3 to 4 carbon atoms containing a double bond; a substituted alkylene bridge containing from 2 to 5 carbon atoms in which the substituent is hydroxy, lower alkoxy, or lower alkyl; or fused aralkylene;

M and M′ when taken with the carbon and nitrogen to which they are respectively attached form a tetrahydroisoquinoline, dihydroindole or pyrrolidine ring;

X is hydrogen; alkyl, alkenyl, or alkynyl of up to 20 carbon atoms; aryl or arylloweralkyl containing from about 7 to 12 carbon atoms; heterocyclic or heterocyclicloweralkyl; cycloalkyl or cycloalkyloweralkyl; or a fused aryl-cycloalkyl group of the formula:

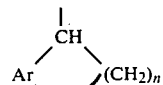

or

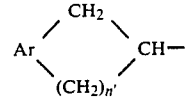

wherein
n = 2, 3 or 4;
n′ = 1, 2 or 3; and
Ar is arylene or substituted arylene containing one or two of the following substituents: halo, $CF_3$, lower alkyl, OH, loweralkoxy, mercapto, amino or sulfamyl; and pharmaceutically-acceptable salts thereof.

A particularly preferred class of compounds are those wherein the substituent M is a fused aryl cycloalkyl as illustrated by the formulas definitive of substituent X. Especially valuable are those compounds in which both X and M are indanyl, particularly 2-indanyl.

These compounds have shown a long-lasting, high potency in testing for angiotensin converting enzyme inhibition.

The most preferred compounds are those in which each of the chiral centers is in the (S)-configuration, sometimes referred to as the L-configuration. The chiral centers are designated in the above formula by an asterisk.

The present new intermediate compounds are useful for the preparation of the aforesaid therapeutic agents especially those in which each of the chiral centers is in the S-configuration. These new intermediates are of the formula

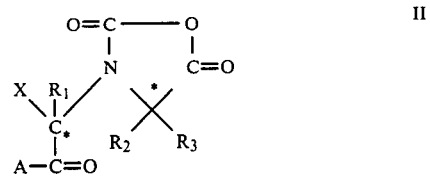   II wherein
A is hydroxy, lower alkoxy, lower alkenoxy, diloweralkylamino lower alkoxy, acylamino lower alkoxy, acyloxy lower alkoxy, aryloxy, arloweralkyloxy, amino, loweralkylamino, diloweralkylamino, aryloweralkylamino, hydroxyamino, or substituted aryloxy, or substituted arloweralkoxy wherein the substituent is methyl, halo or methoxy;

$R_1$, $R_2$, and $R_3$ are each hydrogen, lower alkyl, lower alkenyl, lower alkynyl, aryl, fused aryl-cycloalkyl, aralkyl, cycloalkyl, heterocyclic, substituted alkyl, alkenyl, or alkynyl groups in which the substituents are hydroxy, alkoxy, halo, amino, aminoalkyl, alkylamino, mercapto, or alkylmercapto, substituted cycloalkyl groups in which the substituents are alkyl, halo, haloalkyl, hydroxy, alkylamino, nitro or trifluoromethyl, and substituted aryl and heterocyclic groups in which the substituents are alkyl, hydroxy, alkoxy, hydroxyalkyl, halo, mercapto, alkylmercapto, mercaptoalkyl, haloalkyl, amino, alkylamino, aminoalkyl, nitro, methylenedioxy, or trifluoromethyl;

X is hydrogen, alkyl, alkenyl or alkynyl of up to about 20 carbon atoms, aryl or aryl lower alkyl containing from about 7 to about 12 carbon atoms, heterocyclic or heterocyclic lower alkyl cycloalkyl or cycloalkylalkyl containing up to about 20 carbon atoms, or of the formula:

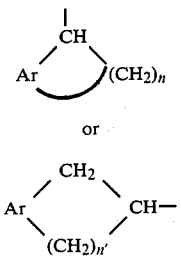

wherein
n=2, 3 or 4;
n'=1, 2 or 3; and
Ar is arylene or mono- or di-substituted arylene in which the substituent is halo, CF$_3$, lower alkyl, OH, lower alkoxy, mercapto, amino or sulfanyl.

The present intermediates form salts with acids and bases and the salts are useful in the isolation and/or purification of the new intermediates.

The alkyl groups in alkyl per se, aralkyl, alkoxy, aminoalkyl, thioalkyl, haloalkyl, and hydroxyalkyl are preferably lower alkyl containing 1 to 6 carbon atoms and may be branched or straight chain.

The alkyl, alkenyl, and alkynyl groups may be substituted with substituents such as hydroxy, alkoxy, halo, amino, alkylamino, mercapto and alkylmercapto.

The cycloalkyl and cycloalkylalkyl groups preferably contain from 3 to 7 carbon atoms in the ring. Such cycloalkyl groups may be substituted with substituents such as alkyl, halo, haloalkyl, hydroxy, hydroxyalkyl, alkoxy, amino, aminoalkyl, alkylamino, trifluoromethyl, and nitro.

The aryl groups may have from 6 to 10 carbons and include phenyl and α- and β-naphthyl. The aryl groups may contain substituents such as alkyl, hydroxy, alkoxy, hydroxyalkyl, mercapto, alkylmercapto, mercaptoalkyl, halo, haloalkyl, amino, alkylamino, aminoalkyl, nitro, methylenedioxy, trifluoromethyl, ureido, and guanidino.

The heterocyclic group per se, and in the heterocyclicalkyl may be saturated, partially saturated or unsaturated and includes such groups as pyridinyl, piperidinyl, morpholinyl, pyrrolyl, pyrrolidinyl, thiomorpholinyl, quinolinyl, isoquinolinyl, tetrahydroquinolinyl, tetrahydroisoquinolinyl, thiazolidinyl, thiazolinyl, thiazolyl, imidazolidinyl, imidazolinyl, imidazolyl, thiophenyl, tetrahydrothiophenyl, furyl, tetrahydrofuranyl, and the like, These heterocyclic groups may also contain substituents as described for the aryl groups above. The heterocyclic group also includes heterocyclic lower alkyl.

The halo groups include fluorine, chlorine, bromine and iodine.

Suitable acid addition salts include inorganic salts such as hydrochloride, phosphate and sulfate; organic carboxylates such as acetate, malate, maleate, fumarate, succinate, citrate, lactate, benzoate, hydroxybenzoate, aminobenzoate, nicotinate, and the like, and organic sulfonic and phosphonic acids such as toluenesulfonic acid.

Suitable acid addition salts include inorganic salts such as hydrochloride, phosphate and sulfate; organic carboxylates such as acetate, malate, maleate, fumarate, succinate, citrate, lactate, benzoate, hydroxybenzoate, aminobenzoate, nicotinate, and the like, and organic sulfonic and phosphonic acids such as toluenesulfonic acid.

Suitable basic salts include alkali and alkaline earth metal salts such as lithium, sodium, potassium, magnesium and calcium and iron, as well as ammonium and quarternary ammonium salts.

The preferred intermediates of the present invention are those in which each of the chiral centers are in the (S)-configuration.

The present new intermediates are reacted under amide-forming conditions with a compound of the formula:

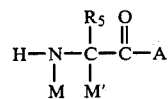

III in which substituents M, M', R$_5$ and A'' are as previously described. A'' is preferably non-reactive under the amide-forming reaction conditions and is most preferably a readily removable group such as benzyloxy which on hydrogenolysis converts to an —OH group.

The conditions required for amide formation simply involve contacting the new intermediates with the aforesaid amines, usually in an organic solvent for efficiency of mixing and contacting the reactants. The reaction proceeds easily at room temperature and even at lower temperatures e.g. as low as 0° C. The use of temperatures higher than room temperature, e.g. up to the reflux temperature of the reaction mixture, may lead to shorter reaction times but also may be accompanied by lower yields of the desired product due to competitive side reactions.

The solvents for the amide formation reaction can include any of a variety of organic solvents including, for example, acetonitrile, tetrahydrofuran, dioxane, methylene chloride, ethylene chloride, and the like. Mixtures of solvents can also be employed.

The acid and base salts of the present new compounds can be formed using standard procedures. Often, they are formed in situ during the preparation of the present new amido amino acids.

The present new compounds are prepared by reacting phosgene (COCl$_2$) with the corresponding amino acid:

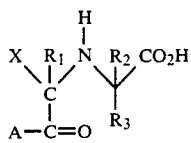

wherein X, $R_1$, $R_2$ and $R_3$ are as hereindescribed and A has the same meaning as hereindescribed excepting hydroxy, and is preferably lower alkoxy or benzyloxy. The reaction is carried in a reaction solvent by addition of phosgene to a mixture of the starting amino acid, conveniently at room temperature where the reaction proceeds smoothly. to shorten the reaction time, the reaction mixture can be heated to reflux after phosgene addition is completed and heating continued to assure completeness of reaction. In general, the reaction can be conducted at temperatures of from 0° up to the reflux temperature of the reaction mixture for a period of from about 0.5 to 3-4 hours. Usually, excess phosgene is employed to assure high conversion yields, for example an excess of 10% and higher.

The product can be isolated using standard procedures, or the concentrated reaction mixture after removal of excess phosgene can be used without isolation and purification of the carboxyanhydride product.

The use of the present new carboxy anhydride intermediates is of particular value in the production of the aforesaid therapeutic agents, particularly those which are difficult to produce in significant yield using ordinary amide formation reactions. The present new intermediates produce significantly higher yields of the desired products than otherwise attainable using, for example, carbodiimide synthesis of the same final therapeutic products.

The following examples further illustrate the invention.

EXAMPLE 1

N-[1-(S)-Ethoxycarbonyl-3-phenylpropyl]-(S)-alanyl-N-carboxyanhydride

N-[1-(S)-Ethoxycarbonyl-3-phenylpropyl]-(S)-alanine (5.0 g, 17.9 mmole) was suspended in dry THF (25 ml) and then placed under nitrogen. An excess of phosgene (12.5% in toluene) was added portionwise. The resulting mixture was stirred for five minutes at room temperature and then heated to a gentle reflux for the two and a half hours. All material dissolved upon the first addition of phosgene. The solvent was evaporated and the residue was placed under high vacuum (oil pump) upon which time the N-carboxyanhydride (NCA) crystallized. The N-carboxyanhydride was used directly in the next reaction without further purification.

EXAMPLE 2

A. tert-Butyl N-(2,3-dehydro-1H-inden-2-yl)glycinate hydrochloride

Acetonitrile (800 mL) was added to 2-amino indan hydrochloride (50 g, 0.295 mole) followed by the addition of water (100 mL) and concentrated ammonium hydroxide (100 mL). To the resulting stirring solution tert-butyl bromacetate (60 g, 0.308 mole) in acetonitrile (150 mL) was added dropwise at room temperature. The resulting mixture was stirred overnight at room temperature. The acetonitrile was evaporated on a rotary evaporator and then water was added to the residue and the product was extracted several times into methylene chloride. The combined methylene chloride extract was washed twice with water, dried over magnesium sulfate, filtered and evaporated to afford the crude product as a tan oil. The crude product was purified by silica-gel chromatography (chloroform). The desired fractions were concentrated and the hydrochloride was prepared with ether-hydrochloric acid to afford tert-butyl N-(2,3-dehydro-1H-inden-2-yl)glycinate hydrochloride as a colorless solid (60 g, 72%); m.p. 175° C.; mass spectra (CI): 248 (M+1, 100%).

B. tert-Butyl N-[1-(S)-ethoxycarbonyl-3-phenylpropyl]-(S)-alanyl-N-(2,3-dehydro-1H-inden-2-yl)glycinate To crude N-[1-(S)-ethoxycarbonyl-3-phenylpropyl]-(S)-alanyl-N-carboxyanhydride, which had been prepared from 5 grams of the corresponding (SS)-acid, in methylene chloride (100 mL) was added tert-butyl N-(2,3-dehydro-1H-inden-2-yl)glycinate (5.5 g, 22.3 mmole). The resulting solution was stirred overnight at room temperature. The solvent was evaporated and the residue was passed through a short silica-gel column (CHCl$_3$) to remove unwanted polar material. The desired fractions were combined and concentrated and then ether saturated with anhydrous hydrogen chloride was added to the residue in order to precipitate unreacted tert-butyl N-(2,3-dehydro-1H-inden-2-yl)glycinate hydrochloride. The hydrochloride was filtered and washed with cold diethyl ether. Methylene chloride and water were added to the filtrate. The aqueous layer was basified to pH 8-9 with concentrated ammonium hydroxide. The layers were separated and the aqueous layer was extracted two more times with methylene chloride. The combined organic extract was washed twice with water, dried over magnesium sulfate, filtered and evaporated to give the desired product as a yellow oil (7.4 g, 81.4%); mass spectra (CI): 509 (M+1, 100%).

C. N-[1-(S)-Ethoxycarbonyl-3-phenylpropyl]-(S)-alanyl-N-(2,3-dehydro-1H-inden-2-yl)glycine hydrochloride To tert-butyl N-[1-(S)-ethoxycarbonyl-3-phenylpropyl]-(S)-alanyl-N-(2,3-dehydro-1H-inden-2-yl)glycinate (1.4 g, 2.75 mmole) was added P-dioxane (35 mL) which had been saturated with anhydrous hydrogen chloride. The resulting solution was stirred for two and a half hours at room temperature and then the solvent was evaporated to afford a colorless solid. Anyhdrous diethyl ether was added to the residue and the product was filtered and washed with a small amount of ether to give N-[1-(S)-ethoxycarbonyl-3-phenylpropyl]-(S)-alanyl-N-(2,3-dehydro-1H-inden-2-yl)glycine hydrochloride (1.1 g, 84.6%) as a colorless solid: m.p. 181° C.; $[\alpha]_D^{EtOH} = +16.44°$: mass spectra (CI): 435.6 (M+1-H$_2$O, 100%).

Analysis calculated for $C_{26}H_{32}N_2O_5 \cdot HCl \cdot \frac{1}{2}H_2O$: C, 62.70; H, 6.68; N, 5.63. Found: C, 62.91; H, 6.70; N, 5.47.

EXAMPLE 3

A. tert-Butyl-N-(3-pyridyl)glycinate

Acetonitrile (300 mL) was added to 3-aminomethylpyridine (21.6 g, 0.2 mole) followed by the addition of water (20 mL) and concentrated ammonium hydroxide (20 mL). To the resulting stirred solution tert-butyl bromoacetate (39 g, 0.2 mole) in acetonitrile (75 mL) was added dropwise. The resulting mixture was stirred overnight at room temperature. The acetonitrile was evaporated on a rotary evaporator and then water was added to the residue and the product was extracted several times into methylen chloride. The combined methylene chloride extract was washed twice with wateer, dried over magnesium sulfate, filtered and evaporated to afford the crude product. The crude product was pjurified by silica-gel chromatography (chloroform). The desired fractions were concentrated and the hydrochloride was prepared by the dropwise addition of ether which had been saturated with anhydrous hydrogen chloride to give a colorless solid (31 g, 61%); m.p. 142° C.

Analysis calculated for $C_{12}H_{18}N_2O_2 \cdot HCl$: C, 55.70; H, 7.40; N, 10.83. Found: C, 55.11; H, 7.19; N, 10.50.

B.
tert-Butyl-N-[1-(S)-ethoxycarbonyl-3-phenylpropyl]-(S)-alanyl-N-(3-pyridyl)glycinate dihydrochloride To crude N-[1-(S)-ethoxycarbonyl-3-phenylpropyl]-(S)-alanyl-N-carboxyanhydride (1.5 g, 4.92 mmole) in methylene chloride (25 mL) was added tert-butyl-N-(3-pyridyl) glycinate (1.4 g, 6.3 mmole). The resulting solution was heated to 50° C. for 16 hours. The solvent was evaporated and the residue was chromatographed over silica-gel using ethylacetate/n-hexane (3:6) as eluent. The desired fractions were combined and concentrated to give the desired product as a pale yellow gum. The product was dissolved in the minimum amount of ether and then with sitrring ether which had been saturated with anhydrous hydrogen chloride was added dropwise. The precipitate was filtered and washed with cold ether to give the desired dihydrochloride as a colorless solid (2.1 g, 82%): m.p. 76° C.; $[\alpha]_D^{CHCl_3} = +50.99°$; $[\alpha]_{546}^{CHCl_3} = +61.36°$; $[\alpha]_{436}^{CHCl_3} = +109.64°$; $[\alpha]_{365}^{CHCL_3} = = -178.26°$; mass spectra (CI): 484.9 (M+1, 100%).

Analysis calculated for $C_{27}H_{37}N_3O_5 \cdot 2HCl$: C, 54.68; H, 6.29; N, 7.09. Found: C, 54.59; H, 6.46; N, 7.32.

C.
N-[1-(S)-Ethoxycarbonyl-3-phenylpropyl)]-(S)-Alanyl-N-(3-pyridyl)glycine dihydrochloride To tert-butyl N-[1-(S)-ethoxycarbonyl]-(S)-alanyl-N-(3-pyridyl)glycinate dihydrochloride (0.5 g, 0.989 mmole) was added p-dioxane (20 mL) which had been saturated with anhydrous hydrogen chloride. The resulting mixture was stirred for three hours at 45° C. and then the solvent was evaporated. To the residue was added diethyl ether after which the product crystallized as a colorless solid. The solid was filtered and washed with cold anhydrous ether (0.413 g, 93%): m.p. 77°; $[\alpha]_{436}^{EtOH} = +14.04$; $[\alpha]_{578}^{EtOH} = +14.67°$; $[\alpha]_{546}^{EtOH} = +16.88$; $[\alpha]_{436}^{EtOH} = +20.32°$; $[\alpha]_{365}^{EtOH} = +7.49°$; mass spectra (CI): 410.1 (M+1-H$_2$O, 100%).

EXAMPLE 4

A. tert-Butyl N-(β-phenethyl)glycinate

Acetonitrile (600 mL) was added to β-phenethylamine (50 g, 0.413 mole) followed by the addition of water (50 mL) and concentrated ammonium hydroxide (50 mL). To the resulting solution tert-butyl bromoacetate (67.3 g, 0.413 mole) in acetonitrile (100 mL) was added dropwise at room temperature. The resulting mixutre was stirred overnight at room temperature. The acetonitrile was evaporated on a rotary evaporator and then water was added to the residue and the product was extracted several times into methylene chloride. The combined methylene chloride extract was washed twice with water, dried over magnesium sulfate, filtered and evaporated to afford the crude product as a tan oil.

B. tert-Butyl N-[1-(S)-ethoxycarbonyl-3-phenylpropyl]-(S)-alanyl-N-(β-phenethyl)glycinate To N-[1-(S)-ethoxycarbonyl-3-phenylpropyl]-(S)-alanyl-N-carboxyanhydride (6.50 g, 21.3 mmole) in methylene chloride (30 mL) was added tert-butyl N-β-phenethyl)glycine (5.0 g, 21.3 mmole). The resulting solution was stirred at room temperature overnight. The solvent was evaporated and the residue was chromatographed over silica-gel using ethyl acetate/n-hexane (1:2) as eluent. The desired fractions were combined and concentrated to give the product as a pale yellow gum (6.2 g, 69.7%) which was used in the next reaction without further purification.

C.
N-[1-(S)-Ethoxycarbonyl-3-phenylpropyl]-(S)-alanyl-N-(β-phenethyl)glycine hydrochloride To tert-butyl N-[1-(S)-ethoxycarbonyl-3-phenylpropyl]-(S)-alanyl-N-(β-phenethyl)glycinate (2.0 g, 4.03 mmole) was added p-dioxane (50 mL) which had been saturated with anhydrous hydrogen chloride. The resulting solution was stirred at room temperature for four hours and then the solvent was evaporated to afford a colorless powder. Ether was added to the residue and the powder was filtered and washed with a small amount of cold ether (1.81 g, 94%): m.p. 72° C.; $[\alpha]_D^{CHCl_3} = +10.95°$; mass spectra (CI): 423 (M+1-H$_2$O, 100%).

Analysis calculated for $C_{25}H_{32}N_2O_5 \cdot 2HCl \cdot \frac{1}{2}H_2O$: C, 61.78; H, 7.05; N, 5.77. Found: C, 61.37; H, 6.71; N, 5.15.

EXAMPLE 5

Benzyl N-(1-ethoxycarbonyl-3-phenylpropyl)-L-alanyl-N-(2,3-dehydro-1H-inden-5-yl)glycinate N-(1-ethoxycarbonyl-3-phenylpropyl)-L-alanine (SS) (447 mg, 1.6 mmole) was combined with p-dioxane 20 mL containing excess dissolved phosgene. The mixture was refluxed for four hours, during which all solids dissolved. After cooling to room temperature, the solution was concentrated in vacuo, dioxane was added and the solution was concentrated. The residual oil was used without further purification.

The above N-carboxyanhydride (NCA) (0.6 mmole) and benzyl N-(2,3-dehydro-1H-inden-5-yl)glycinate (169 mg, 0.6 mmole) were refluxed 8 hours in methylene chloride (5 mL) then cooled and concentrated to an oil. The product was purified by preparative thin-layer chromatography using as a developing solvent hexane/ethyl acetate; 3.5/1.5, R$_f$ 0.34 (silica gel, hexane/ethyl acetate; 3.5/1.5).

Using the procedure of Example 1, the following compounds are prepared:
N-[1-(S)-Ethoxycarbonyl-3-(2,3-dehydro-1H-inden-2-yl)methyl]-S-alanyl-N-carboxy-anhydride
N-[1-(S)-Ethoxycarbonyl-3-(2,3-dehydro-1H-inden-3-yl)methyl]-S-alanyl-N-carboxy-anhydride
and these are converted to similar end products using the procedures of Examples 2-5.

What is claimed is:
1. A compound of the formula:

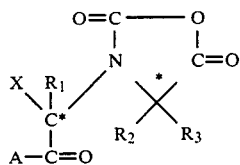

wherein

A is hydroxy, lower alkoxy, lower alkenoxy, diloweralkylamino lower alkoxy, acylamino lower alkoxy, acyloxy lower alkoxy, lower aryloxy, lower arloweralkyloxy, amino, loweralkylamino, diloweralkylamino, aryloweralkylamino, hydroxyamino, or substituted lower aryloxy, or substituted lower arloweralkoxy wherein the substituent is methyl, halo or methoxy;

R₁, R₂ and R₃ are each hydrogen, lower alkyl, lower alkenyl, lower alkynyl, lower aryl, fused lower aryllowercycloalkyl, lower arloweralkyl, lower cycloalkyl, substituted lower alkyl, lower alkenyl, or lower alkynyl groups in which the substituents are hydroxy, lower alkoxy, halo, amino, aminoloweralkyl, lower alkylamino, mercapto, or lower alkylmercapto, substituted lower cycloalkyl groups in which the substituents are lower alkyl, halo, haloloweralkyl, hydroxy, lower alkylamino, nitro or trifluoromethyl, and substituted lower aryl groups in which the substituents are lower alkyl, hydroxy, lower alkoxy, hydroxyloweralkyl, halo, mercapto, lower alkylmercapto, mercaptoloweralkyl, haloloweralkyl, amino, lower alkylamino, aminoloweralkyl, nitro, methylenedioxy, or trifluoromethyl;

X is hydrogen, lower alkyl, lower alkenyl or lower alkynyl of up to about 20 carbon atoms, lower aryl or lower aryl lower alkyl containing from about 7 to about 12 carbon atoms, heterocyclic or heterocyclic lower alkyl cycloalkyl or cycloalkylalkyl containing up to about 20 carbon atoms, or of the formula:

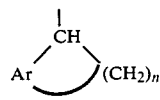

or

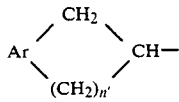

wherein n = 2, 3 or 4;
n' = 1, 2 or 3; and

Ar is arylene or mono- or di-substituted arylene in which the substituent is halo, CF₃, lower alkyl, OH, lower alkoxy, mercapto, amino or sulfanyl, it being further provided that the heterocyclic group is selected from the group consisting of pyridinyl, piperidinyl, morpholinyl, pyrrolyl, pyrrolidinyl, thiomorpholinyl, quinolinyl, isoquinolinyl, tetrahydroquinolinyl, tetrahydroisoquinolinyl, thiazolidinyl, thiazolinyl, thiazolyl, imidazolidinyl, imidazolinyl, imidazolyl, thiophenyl, tetrahydrothiophenyl, furyl and tetrahydrofuranyl and arylene is selected from the group consisting of phenyl, α-naphthyl and β-naphthyl.

2. The compound according to claim 1 wherein X is aryl lower alkyl containing from about 7 to about 12 carbon atoms.

3. The compound according to claim 1 wherein X is of the formula

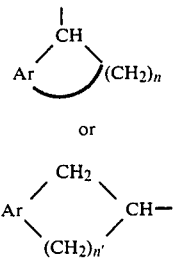

wherein
n = 2;
n' = 1; and
Ar is arylene.

4. The compound according to claim 1 wherein X is phenethyl.

5. The compound according to claim 1 wherein X is 2,3-dehydro-1H-inden-3-yl.

6. The compound according to claim 1 wherein X is 2,3-dehydro-1H-inden-2-yl.

7. N-[1-(S)-Ethoxycarbonyl-3-phenylpropyl]-(S)-alanyl-N-carboxyanhydride.

8. N-[1-(S)-Ethoxycarbonyl-3-(2,3-dehydro-1H-inden-2-yl)methyl]-S-alanyl-N-carboxyanhydride.

9. N-[1-(S)-Ethoxycarbonyl-3-(2,3-dehydro-1H-inden-3-yl)methyl]-S-alanyl-N-carboxyanhydride.

10. The compound according to claim 1 wherein X is 4-morpholinyl.

11. The compound according to claim 1 wherein X is 1-pyrrolidinyl.

* * * * *